United States Patent [19]
Kohnert et al.

[11] Patent Number: 5,366,730
[45] Date of Patent: Nov. 22, 1994

[54] STABILIZED COMPOSITIONS HAVING HUMAN TISSUE TYPE PLASMINOGEN ACTIVATOR ENZYMATIC ACTIVITY

[75] Inventors: Ulrich Kohnert, Habach; Rainer Rudolph, Weilheim, both of Germany

[73] Assignee: Boehringer Mannheim GmbH, Mannheim-Waldhof, Germany

[21] Appl. No.: 43,619

[22] Filed: Apr. 6, 1993

Related U.S. Application Data

[63] Continuation-in-part of Ser. No. 720,796, Jul. 19, 1991, abandoned.

[30] Foreign Application Priority Data

Dec. 2, 1989 [DE] Germany .................. 3942145

[51] Int. Cl.$^5$ ............... A61K 37/547; A61K 37/553; A61K 37/48; C12N 9/50
[52] U.S. Cl. ................ 424/94.64; 435/219; 424/94.1
[58] Field of Search ............ 435/188, 219, 226; 424/94.1, 94.64

[56] References Cited

U.S. PATENT DOCUMENTS

| | | | |
|---|---|---|---|
| 4,568,544 | 2/1986 | Hasegawa et al. | 424/94.1 |
| 4,898,826 | 2/1990 | Duffy et al. | 435/219 |
| 4,980,165 | 12/1990 | Isaacs et al. | 424/94.64 |
| 5,068,106 | 11/1991 | Pâques et al. | 424/94.64 |
| 5,095,034 | 3/1992 | Kato et al. | 514/822 |

FOREIGN PATENT DOCUMENTS

| | | |
|---|---|---|
| 0029724 | 6/1981 | European Pat. Off. . |
| 0211592 | 2/1987 | European Pat. Off. . |
| 0264887 | 4/1988 | European Pat. Off. . |
| 0098688 | 6/1984 | Japan . |

OTHER PUBLICATIONS

*Methods of Enzymology*—vol. 182, 1990 Academic Press Inc. Deutscher, Murray P., *Guide to Protein Purification*, Chap. 8, "Maintaining Protein Stability", pp. 83–86.

Ranby et al., "Blood Collection in Strong Acidic Citrate anticoagulant used in a study of dietary influence on Basal & Pa Activity" Thrombosis and Haemostasis, 62(3), pp. 917–922 (1989).

*Primary Examiner*—Douglas W. Robinson
*Assistant Examiner*—Kristin Larson
*Attorney, Agent, or Firm*—Felfe & Lynch

[57] ABSTRACT

Pharmaceutical preparation of a protein with t-PA activity with an enzymatic activity of at least 0.25 MU/ml. and a pH value of 4.5 to 9 which contains a substance of the group citric acid, ascorbic acid, 2-oxo-glutaric acid, fumaric acid, Tris and EDTA in a concentration of at least 0.2 mole/l., as well as a medicament based on a protein with t-PA activity and processes for its preparation.

20 Claims, No Drawings

STABILIZED COMPOSITIONS HAVING HUMAN TISSUE TYPE PLASMINOGEN ACTIVATOR ENZYMATIC ACTIVITY

This application is a continuation-in-part application of U.S. Ser. No. 07/720,796, which was filed on Jul. 19, 1991, now abandoned.

Human tissue plasminogen activator (t-PA) possesses great therapeutic importance in the dissolving of blood coagula, e.g. in the case of heart infarcts. t-PA acts on the blood coagulation cascade by the activation of plasminogen to plasmin. Plasmin in turn dissolves fibrin, the main component of the protein matrix of coagulated blood.

Natural t-PA is composed of several functional domains F, G, K1, K2 and P. The domain P contains the proteolytically active region which brings about the cleavage of plasminogen to plasmin. Recombinant preparations of t-PA or of t-PA mutants, in which some of the domains F, G, K1 and K2 are deleted, in eukaryotic and prokaryotic cells is already known. In contradistinction to natural t-PA, t-PA derivatives are synthesized from prokaryotes in non-glycosylated form.

Proteins with t-PA activity dissolve in only low concentration in the buffers usually employed for the solubilization of proteins, such as e.g. 50 mmole/l. Na citrate, 50 mmole/l. phosphate or physiological NaCl. However, for use as therapeutic active material, proteins with t-PA activity should be present with a comparatively high enzymatic activity of at least 0.25 MU/ml., preferably of 0.25 MU/ml. to 10 MU/ml.

From EP-A 0 217 379, it is known to increase the solubility of t-PA by neutral or slightly alkaline arginine formulations. A disadvantage of this process is, however, the low stability of highly concentrated t-PA under neutral or slightly alkaline conditions.

U.S. Pat. No. 4,777,043 discloses a pharmaceutical composition with human t-PA and a pharmaceutically compatible arginium ion-containing buffer with a chloride ion concentration of up to 0.3 mole/l. EP-A 0 156 169, EP-A 0 303 351 and EP-A 0 297 294 disclose further possibilities of solubilizing proteins with t-PA activity in buffers by means of amino acids, their salts, derivatives and homologues. Furthermore, t-PA can be stabilized by addition of gelatin according to EP-A 0 123 304, by addition of albumin according to EP-A 0 122 940 or by addition of a polysulphuric acid ester of a saccharide or of a sulphated sugar according to EP-A 0 198 321. PCT/US88/04402 discloses a process for the increasing t-PA solubility, wherein one uses an aqueous medium with a basic amino acid, especially arginine, in a concentration of 0.02 to 0.2 mole/l., together with a citric acid group in a concentration of 0.02 to 0.08 mole/l. at a pH value of 5 to 8.

However, these various compositions are not generally suitable for all proteins with t-PA properties. In particular, it was ascertained that non-glycosylated t-PA, non-glycosylated t-PA muteins and glycosylated t-PA possess solubility properties differing greatly from one another.

Consequently, it is the aim of the invention to develop a pharmaceutical composition which contains glycosylated and non-glycosylated t-PA or t-PA mutants with an activity of more than 0.25 MU/ml., whereby the t-PA is to be stable over a comparatively long period of time.

The task according to the invention is solved by a pharmaceutical preparation of a protein with t-PA activity in a concentration of at least 0.25 MU/ml. with a pH value of 4.5 to 9, whereby this composition contains a substance of the group citric acid, ascorbic acid, 2-oxoglutaric acid, fumaric acid, Tris and EDTA in a concentration of at least 0.2 mole/l but preferably does not contain any of histidine, creatinine, lysine or ornithine.

Preferred is a concentration of the above-mentioned substances of 0.2 to 1 mole/l. An especially preferred concentration range is 0.3 to 1 mole/l.

Suitable for a composition according to the invention is a pH value between 4.5 and 9, a pH value of 6 to 7.5 is especially preferred.

The phrase protein with t-PA-activity as used herein refers to unmodified t-PA obtained from prokaryotic and eukaryotic organisms, as well as all t-PA mutants. Examples of t-PA mutants are described e.g. by Harris (Protein Engineering, 1 (1987), 449–458).

The composition according to the invention preferably contains native glycosylated t-PA, e.g. from CHO cells. If the preparation according to the invention contains a native glycosylated t-PA, then its enzymatic activity is preferably at least 1.4 MU/ml.

The unit U is a unit of the activity for t-PA according to the definition of the WHO, National Institute for Biological Standards and Control.

Further preferred is a non-glycosylated t-PA from prokaryotes (t-PA pro), which is obtainable according to DE-35 37 708. By t-PA pro, one understands a t-PA which begins with the amino acids −3 (Gly) to +1 (Ser) and ends at 527 (Pro) (nomenclature according to Harris, Protein Engineering, Volume 1 (1987) 449–458). If a preparation according to the invention contains t-PA pro, then its enzymatic activity should amount to at least 0.25 MU/ml.

Further preferred is also a non-glycosylated t-PA mutant with the domains K1, K2 and P, which is designated K1K2P pro (preparation according to DE 39 233.391.1). K1K2P pro begins at amino acid 85–92 and ends at 527 (Pro). If a preparation according to the invention contains K1K2P pro, then its enzymatic activity is to amount to at least 0.4 MU/ml.

Further preferred is a non-glycosylated t-PA mutant with the domains K2 and P, which is designated as K2P pro (preparation according to EP-A 0 382 174). K2P pro begins at one of acids 174–179 and ends with 527 (Pro). K2P pro, as well as K1K2P pro, can contain partly or wholly the amino acids −3 (Gly) to +5 (Ile) according to Harris, supra. If the preparation according to the invention contains K2P pro, then its enzymatic activity preferably amounts to at least 1.4 MU/ml. However, all other t-PA variants from prokaryotes or eukaryotes are also suitable.

In the following a series of especially preferred preparations according to the present invention are set forth.

One formulation contains 300 mmole/l. citric acid/NaOH, pH 6. A further formulation contains 300 mmole/l. ascorbic acid, pH 6. Yet, a further formulation contains 300 mmole/l. 2-oxoglutaric acid, pH 6. Yet, a further formulation contains 300 mmole/l. EDTA, pH 6. Still another further formulation contains 300 mmole/l. fumaric acid/NaOH, pH 6. Yet, a further formulation contains 1 mole/l. Tris/HCl, pH 7.2.

Finally, a subject of the invention is a medicament based on a protein with t-PA activity as active material in solution or as lyophilisate the given active materials and possibly also further pharmaceutically compatible additive, adjuvant, carrier and filling materials.

The pharmaceutical preparations according to the invention are preferably used as injection or infusion solutions. This can take place in that a solution ready for injection is made available which possesses the composition according to the invention. However, it is also possible to make available pharmaceutical preparations in the form of lyophilisates. These are then reconstituted with per se known agents or solutions suitable for injection purposes. As injection medium, water is preferably used which contains the additives usual in the case of injection solutions, such as stabilizing agents, solubilizing agents, buffers and isotonic additives, for example a physiological NaCl concentration. Examples of such additives are mannitol, tartrate, or citrate buffers; complex formers such as ethylenediaminetetraacetic acid and its non-toxic salts; and viscosity regulating agents such as high molecular polymers, an example of which is liquid polyethylene oxide. Liquid carrier materials for injection solutions must be sterile and are preferably filled into ampules.

Finally, the present invention also comprises the use of glycosylated proteins with t-PA activity for the preparation of pharmaceutical preparations according to the invention.

The following Examples are to explain embodiments of the invention.

EXAMPLE 1

Influence of various substances on the solubility of a non-glycosylated t-PA mutant with the domain composition K2P In this Example, the solubility of K2P pro (preparation according to EP-A 0 382 174) in various buffer solutions is described. As is to be gathered from Table 1, K2P pro dissolves in the buffer solutions set out with a distinctly higher activity than 1.4 MU/ml.

Carrying Out 170 ml. purified K2P pro (dissolved in 0.5 mole/l. arginine/phorphoric acid pH 7.2) is concentrated by ultra-filtration over an Amicon YM 10 membrane. In each case, 1 ml. of the concentrate is dialyzed against the buffers set out in Table 1. After centrifuging the samples, the enzymatic activity is measured in the supernatant.

The enzymatic activity is given as volume activity in MU/ml. and as total activity in MU.

The measurement of the t-PA activity can be determined in the usual way by cleavage of a chromogenic substrate (H. Lill, ZGIMAL, 42, (1987), 478–486). The unit U is one unit of the activity for t-PA according to the definition of the WHO, National Institute for Biological Standards and Control.

TABLE 1

| buffer | activity MU/ml. | MU |
|---|---|---|
| 0.3 mole/l. citric acid/NaOH, pH 6 | 2.23 | 2.05 |
| 0.3 mole/l. ascorbic acid/NaOH, pH 6 | 1.68 | 1.95 |
| 1 mole/l. Tris/HCl, pH 7.2 | 8.76 | 5.8 |
| 0.3 mole/l. EDTA/NaOH, pH 6 | 1.95 | 1.95 |
| 0.3 mole/l. 2-oxoglutaric acid, pH 6 | 2.64 | 3.17 |
| 0.3 mole/l. fumaric acid/NaOH, pH 6 | 1.85 | 4.08 |

EXAMPLE 2

Solubility of K1K2P pro

Purified K1K2P pro (dissolved in 0.5 mole/l. arginine/$H_3PO_4$) is concentrated by ultrafiltration over a YM 10 membrane (Amicon). In each case, 0.5 ml. of the concentrate (activity: 3.5 MU/ml.) is dialyzed against the buffer set out in Table 2. After centrifuging the samples, the enzymatic activity is measured in the clear supernatant.

The enzymatic activity is given as volume unit in MU/ml. and total activity in MU.

The measurement of the t-PA activity can be determined in the usual way by cleavage of a chromogenic substrate (H. Lill, ZGIMAL, 42 (1987), 478–486). The unit U is a unit of activity according to the definition of the WHO, National Institute for Biological Standards and Control.

TABLE 2

| buffer | activity MU/ml. | MU |
|---|---|---|
| 1 mole/l. Tris/HCl, pH 7.2 | 1.65 | 1.07 |

EXAMPLE 3

Solubility of tPA pro

Purified tPA pro (dissolved in 0.5 mole/l. arginine/$H_3PO_4$) is concentrated by ultrafiltration over a YM 10 membrane (Amicon). In each case, 1 ml. of the concentrate (activity: 2.4 MU/ml.) is dialyzed against the buffers set out in Table 3. After centrifuging the samples, the enzymatic activity is measured in the clear supernatant.

The enzymatic activity is given as volume unit in MU/ml. and as total activity in MU.

The measurement of the tPA activity can be determined in the usual way by cleavage of a chromogenic substrate (H. Lill, ZGIMAL, 42 (1987), 478–486). The unit U is a unit of activity according to the definition of the WHO, National Institute for Biological Standards and Control.

TABLE 3

| buffer | activity MU/ml. | MU |
|---|---|---|
| 0.3 M citric acid/NaOH, pH 6 | 0.29 | 0.16 |
| 1 M Tris/HCl, pH 7.2 | 2.15 | 1.07 |

EXAMPLE 4

Solubility of CHO-tPA

Purified CHO-tPA (dissolved in 0.5 mole/l. arginine/$H_3PO_4$) is concentrated by ultrafiltration over a YM 10 membrane (Amicon). In each case, 1 ml. of the concentrate (activity: 6.6 MU/ml.) is dialyzed against the buffers set out in Table 4. After centrifuging the samples, the enzymatic activity is measured in the clear supernatant.

The enzymatic activity is given as volume units in MU/ml. and as total activity in MU.

The measurement of the tPA activity can be determined in the usual way by cleavage of a chromogenic substrate (H. Lill, ZGIMAL, 42 (1987) 478–486). The unit U is a unit of activity according to the definition of the WHO, National Institute for Biological Standards.

TABLE 4

| buffer | activity MU/ml. | MU |
|---|---|---|
| 1 M Tris/HCl, pH 7.2 | 6.16 | 6.49 |
| 0.3 M citric acid/NaOH, pH 6 | 4.44 | 4.44 |

We claim:

1. A pharmaceutical composition consisting essentially of a protein having human tissue type plasminogen activator (t-PA) enzymatic activity of at least 0.25 MU/ml and a substance selected from the group consisting of ascorbic acid, Tris and EDTA, said substance being present in a concentration of from 0.3 mole/l to 1 mole/l, said composition having a pH of from 4.5 to 9.

2. Pharmaceutical composition of claim 1, wherein said protein is tPA derivative K2P, is non-glycosylated, and has enzyme activity of at least 1.4 MU/ml.

3. Pharmaceutical composition of claim 1, wherein said protein is tPA derivative K1K2P, is non-glycosylated, and has enzyme activity of at least 0.4 MU/ml.

4. Pharmaceutical composition of claim 1, wherein said protein is a non-glycosylated t-PA pro derivative.

5. Pharmaceutical composition of claim 1, wherein said protein is glycosylated t-PA with enzymatic activity of at least 1.4 MU/ml.

6. Pharmaceutical composition of claim 1, having a pH of 6.

7. Pharmaceutical composition of claim 6, containing ascorbic acid at a concentration of 300 mmol/liter.

8. Pharmaceutical composition of claim 6, containing EDTA at a concentration of 300 mmol/liter.

9. Pharmaceutical composition of claim 1, having a pH of 7.2 and containing Tris at a concentration of 1 mole/liter.

10. A pharmaceutical composition consisting essentially of a protein having human tissue type plasminogen activator (t-PA) enzymatic activity of at least 0.25 MU/ml and a substance selected from the group consisting of citric acid, 2-oxo-glutaric acid and fumaric acid, wherein said substance is present in a concentration of from 0.3 mole/l to 1 mole/l, said composition having a pH of from 6.0 to 7.5.

11. Pharmaceutical composition of claim 10, containing citric acid at a concentration of 300 mmol/liter.

12. Pharmaceutical composition of claim 10, containing 2-oxo-glutaric acid at a concentration of 300 mmol/liter.

13. Pharmaceutical composition of claim 10, wherein said protein is tPA derivative K2P, is non-glycosylated, and has enzyme activity of at least 1.4 MU/ml.

14. Pharmaceutical composition of claim 10, wherein said protein is tPA derivative K1K2P, is non-glycosylated, and has enzyme activity of at least 0.4 MU/ml.

15. Pharmaceutical composition of claim 10, wherein said protein is a non-glycosylated t-PA pro derivative.

16. Pharmaceutical composition of claim 10, wherein said protein is glycosylated t-PA with enzymatic activity of at least 1.4 MU/ml.

17. Pharmaceutical composition of claim 10, having a pH of 6.

18. A pharmaceutical composition consisting essentially of a protein having human tissue type plasminogen activator (t-PA) enzymatic activity of at least 0.25 MU/ml and a substance selected from the group consisting of ascorbic acid, Tris and EDTA, said substance being present in a concentration of from 0.3 mole/l to 1 mole/l, said composition having a pH of from 6.0 to 9.

19. A pharmaceutical composition consisting essentially of a protein having human tissue type plasminogen activator (t-PA) enzymatic activity of at least 0.25 MU/ml, a substance selected from the group consisting of ascorbic acid, Tris, and EDTA, said substance being present in a concentration of from 0.3 mole/l to 1 mole/l, and a filler or carrier, said composition having a pH of from 4.5 to 9.

20. A pharmaceutical composition consisting essentially of a protein having human tissue plasminogen activator (t-PA) enzymatic activity of at least 0.25 MU/ml, a substance selected from the group consisting of citric acid, 2-oxo-glutaric acid and fumaric acid, wherein said substance is present in a concentration of from 0.3 mole/l to 1 mole/l, and a filler or carrier, said composition having a pH of from 6.0 to 7.5.

* * * * *

UNITED STATES PATENT AND TRADEMARK OFFICE
CERTIFICATE OF CORRECTION

PATENT NO. : 5,366,730
DATED : November 22, 1994
INVENTOR(S) : Kohnert et al.

It is certified that error appears in the above-indentified patent and that said Letters Patent is hereby corrected as shown below:

<u>ON THE COVER PAGE</u>

Under "Foreign Publication Priority Data", before "[DE]", delete "Dec. 2, 1989", and substitute with --Dec. 20, 1989--.

Under "Foreign Application Priority Data", add the following line:

--Dec. 19, 1990 [PCT] ............ PCT/EP90/02249--.

Signed and Sealed this

Twenty-seventh Day of June, 1995

Attest:

BRUCE LEHMAN

*Attesting Officer*  *Commissioner of Patents and Trademarks*